United States Patent
Mocnik et al.

(10) Patent No.: US 9,804,082 B2
(45) Date of Patent: *Oct. 31, 2017

(54) METHOD FOR AUTOMATIC PERFORMANCE DIAGNOSIS AND CALIBRATION OF A PHOTOMETRIC PARTICLE ANALYZER

(71) Applicant: Magee Scientific Corporation, Berkeley, CA (US)

(72) Inventors: Grisa Mocnik, Ljubljana (SI); Anthony D. A. Hansen, Berkeley, CA (US); Jeffrey R. Blair, San Francisco, CA (US)

(73) Assignee: Magee Scientific Corporation, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/928,979

(22) Filed: Oct. 30, 2015

(65) Prior Publication Data

US 2016/0216200 A1 Jul. 28, 2016

Related U.S. Application Data

(63) Continuation-in-part of application No. 14/690,288, filed on Apr. 17, 2015, now abandoned, which is a continuation of application No. 13/413,580, filed on Mar. 6, 2012, now Pat. No. 9,018,583.

(60) Provisional application No. 61/450,536, filed on Mar. 8, 2011.

(51) Int. Cl.
*G01N 21/27* (2006.01)
*G01N 15/06* (2006.01)
*G01N 21/15* (2006.01)

(52) U.S. Cl.
CPC ....... *G01N 21/274* (2013.01); *G01N 15/0618* (2013.01); *G01N 15/0625* (2013.01); *G01N 2021/157* (2013.01); *G01N 2201/0627* (2013.01)

(58) Field of Classification Search
CPC ............. G01N 21/274; G01N 15/0618; G01N 2201/0627; G01N 2201/068; G01N 2201/127
See application file for complete search history.

(56) References Cited

U.S. PATENT DOCUMENTS

| | | | | |
|---|---|---|---|---|
| 7,038,765 | B2* | 5/2006 | Petzold | G01N 21/47 356/38 |
| 8,319,183 | B2* | 11/2012 | Gunasekaran | G01N 21/3581 250/338.1 |
| 8,411,272 | B2* | 4/2013 | Hansen | G01N 21/4738 356/38 |
| 8,531,671 | B1* | 9/2013 | Hansen | G01N 15/0625 356/38 |
| 2010/0027013 | A1* | 2/2010 | Hansen | G01N 21/4738 356/432 |

(Continued)

*Primary Examiner* — Christine Sung

(57) ABSTRACT

A method is provided for diagnosing the operation of a photometric particle analyzer. The method may determine when the operation is degraded from normal operating conditions, automatically, and the result displayed locally as well as being transmitted to a remote observer. The present invention may be used by optical photometric particle analyzers, or by analyzers that measure other properties of particles collected on filters.

31 Claims, 2 Drawing Sheets

(56) References Cited

U.S. PATENT DOCUMENTS

| | | | |
|---|---|---|---|
| 2010/0111792 A1* | 5/2010 | Nelson | B01J 19/121 423/219 |
| 2010/0306140 A1* | 12/2010 | Verdegan | G01N 15/0205 706/12 |
| 2011/0210271 A1* | 9/2011 | LeBoeuf | G01N 21/645 250/459.1 |

* cited by examiner

METHOD FOR AUTOMATIC PERFORMANCE DIAGNOSIS AND CALIBRATION OF A PHOTOMETRIC PARTICLE ANALYZER

CROSS-REFERENCE TO RELATED APPLICATIONS

This application is a continuation in part of U.S. patent Ser. No. 14/690,288, filed Apr. 17, 2015, which is a continuation of U.S. patent Ser. No. 13/413,580, filed on Mar. 6, 2012, and which issued as U.S. Pat. No. 9,018,583 on Apr. 28, 2015, which claims the benefit of U.S. Provisional Application No. 61/450,536, filed Mar. 8, 2011, the entire contents of which hereby are incorporated by reference herein and made part of this specification.

BACKGROUND OF THE INVENTION

Field of the Invention

The present invention generally relates to calibration methods, and more particularly to a method to automatically diagnose photometric particle analyzers.

Discussion of the Background

There is a class of instruments, often referred to as "photometric particle analyzers" that analyze airborne particles by collecting samples of the particles on a filter, and then sensing the collected particles on the filter. One example of such an instrument is an optical photometric particle analyzer known as an AETHALOMETER® (Magee Scientific Corporation, Berkeley, Calif.). The AETHALOMETER® collects particles suspended in an air stream by continuous filtration of the air through a porous, fibrous substrate, such as a quartz fiber filter. Simultaneously, the optical transmission of the filter is continuously measured by illumination of the upper surface, and detection of the light transmitted through various portions of the filter to its underside.

If the sampled air stream of an AETHALOMETER® contains optically-absorbing particles, the accumulation on the filter will contain a mass of material (including the "Black Carbon" component, denoted "BC") that will absorb some of the incident light, and reduce the amount of light transmitted through the filter. The AETHALOMETER® precisely measures the intensity of light transmitted through the "sensing" portion of filter material, on which particles are collected, and compares this with the intensity of light emanating from the same source but passing through a "reference" portion of the same filter material but which is not subject to the collection of particles. The AETHALOMETER® may function, for example, by using photodetectors to accurately measure the intensity of light transmitted through various portions of an "optical analysis head." The illuminating light is provided by a multiplicity of light-emitting diode (LED) sources emitting at a variety of wavelengths. The ratio of these intensities leads to the calculation of optical absorption, since the common denominator is the intensity of light produced by the source. The relation between optical absorption and mass of BC, determined by separate laboratory techniques, allows the increase in optical absorption between one measurement and the next to be interpreted as the accumulation of a certain amount of BC during the measurement period. Since this material was collected from the flowing air stream, the concentration of BC in the sample air stream can be calculated, given a simultaneous measurement of the air flow rate by a separate sensor. In this way, the AETHALOMETER® offers a real-time measurement of the concentration of BC particles in an air stream.

While the use of photometric particle analyzers is effective, and generally have a linear response, variations of light intensity or detector response can degrade the accuracy of the instruments. There are many different potential sources of error in the use of photometric particle analyzer. Thus, for example, degradation in accuracy can result from contamination of the optics or the light sources, or from changes in the linearity of response of the instrument. There is a need in the art for a method of determining when the performance of a photometric particle analyzer is degraded under such circumstances. Such a method should be compatible with existing instruments, should be easy to implement.

BRIEF SUMMARY OF THE INVENTION

The present invention overcomes the disadvantages of prior art photometric particle analyzers by determining when the operation is degraded from normal operating conditions. Thus, for example, the operation of an instrument may be automatically checked, and the result displayed locally as well as being transmitted to a remote observer. The present invention may be used by optical photometric particle analyzers, or by analyzers that measure other properties of particles collected on filters.

Certain embodiments overcomes the limitations of the prior art by controlling the intensity of light sources at one or at multiple optical wavelengths and using control electronics and hardware. The method requires only added control software and numerical analysis of the measured results. The method produces both a validation of the instrument's analytical performance, as well as a measure of the degree and optical nature of contamination that will permit a determination of the need for intervention, remedy or cleaning.

In certain embodiments, a method is provided to perform an automatic performance diagnosis and calibration of photometric particle analyzers that operate on the principle of measuring the absorption of light transmitted through a deposit of particles collected on a filter.

In certain other embodiments, a method is provided to test the response of the light source and the light detectors of a photometric particle analyzer, and provide a quantitative measure of a standardized response of the instrument that may be used to verify the analytical performance of the instrument. Thus, for example, one method determines the presence of contamination within the optical elements of the instrument, and to enable a tentative identification of the nature of said contamination, and does so with no physical intervention with the instrument.

In yet certain other embodiments, a method is provided to test the response of the light source and the light detectors of a photometric particle analyzer, and provide a quantitative measure of a standardized response of the instrument that may be used to verify the analytical performance of the instrument, where the method may be activated either by remote control or by a predetermined routine internal to the instrument, and the results may be transmitted by a data link to a remote observer or controller, either human or automatic. This permits the automatic external or self-diagnosis of an analyzer that may be located remotely, and allows for human operators or automatic systems to determine the need for intervention, remedy or cleaning.

In certain other embodiments, a method is provided to validate the performance of instruments used for the analysis of the concentration of particles suspended in an air flow stream. The method can provide an indication of any degradation in performance due to internal contamination, and thereby remotely and automatically indicate the need for intervention and service. Both of these actions increase the utility of the instrument, by allowing it to be installed remotely and yet, by means of a data link, have its performance checked by an agent at another location, either human or automatic.

In certain embodiments, a method of testing a photometric particle analyzer is provided. The photometric particle analyzer includes one or more light sources each emitting light at a corresponding wavelength or a corresponding range of wavelengths, where each light source has a controllable intensity, a filter to collect particles, a first light path from the light source through a collecting portion of the filter that may be exposed to particle laden-air to a first sensor that produces a first signal, a second light path from the light source through a reference portion of the filter to a second sensor that produces a second signal, and a third light path from the light source to a third sensor without passing through the filter, where the third sensor produces a third signal. The method includes selecting the number of wavelengths or ranges of wavelengths of the one or more light sources, obtaining a baseline measurement of the first, second, and third signals, where the obtaining obtains with first light path, second light path, and third light path, in the absence of particles, and where the obtaining includes: operating the light sources at the selected number of wavelengths or ranges of wavelengths, and recording the baseline measurement; using the photometric particle analyzer to sample particle-laden air; obtaining a test measurement of the first, second, and third signals for the photometric particle analyzer after using the photometric particle analyzer to sample particle-laden air by: replacing the collecting portion of the filter with a collecting portion that has not been previously used to collect particles, operating the light sources at the selected number of wavelengths or ranges of wavelengths, and recording the test measurement; and generating an output from a comparison of the baseline measurement and the test measurement. The output is a diagnostic of the operation of the photometric particle analyzer.

In certain other embodiments, a method of testing a photometric particle analyzer is provided. photometric particle analyzer has having one or more light sources each emitting light at a corresponding wavelength or a corresponding range of wavelengths, optics, a filter that may collect particulates, and sensors, including a first sensor, a second sensor and a third sensor, and a stored baseline measurement of one or more of the sensors obtained with clean optics and filter between the light source and the one or more sensors. The method includes: selecting the number of wavelengths or ranges of wavelengths of the one or more light sources; providing light from the one or more light sources through a collecting portion of the filter that may be exposed to particle laden-air to the first sensor that produces a first signal; providing light from the one or more light sources through a reference portion of the filter to the second sensor that produces a second signal; providing light from the one or more light sources through the third sensor without passing through the filter, where the third sensor produces a third signal; and generating an output from a comparison of the first signal, the second signal, the third signal and the stored baseline measurement. The output is a diagnostic of one or more of the first signal, the second signal, and the third signal of the photometric particle analyzer.

These features and advantages, together with the various ancillary provisions and features which will become apparent to those skilled in the art from the following detailed description, are attained by the method for automatic performance diagnosis and/or calibration of a photometric particle analyzer of the present invention, preferred embodiments thereof being shown with reference to the accompanying drawings, by way of example only, wherein:

Reference symbols are used in the Figures to indicate certain components, aspects or features shown therein, with reference symbols common to more than one Figure indicating like components, aspects or features shown therein.

DETAILED DESCRIPTION OF THE INVENTION

Various embodiments described herein are directed to methods for operating analytic instruments that permit the identification, characterization, or quantification of one or more constituents of interest, such as particulates. The following description includes a description of an apparatus that is meant to provide an understanding of the methods of the present invention, and is not meant to limit the scope of the invention. In particular, the method of the present invention is described using the example an optical analysis of airborne particles for carbon content, but may be applied to other photometric analyzers.

The various embodiments described above thus provide a means whereby a photometric particle analyzer can be controlled to perform an automatic self-diagnosis of the optics, yielding quantitative numerical results. The diagnostic procedure may be instigated either manually, by an operator at the site of the instrument; remotely, by command transmitted by communication; or automatically on a programmed time sequence. The results of the diagnostic procedure may be displayed locally to an operator at the site of the instrument; may be transmitted to a remote receiver for examination elsewhere, either by expert automatic systems or by human operators; or may be stored in a data file retained within the instrument.

Further, the raw, unprocessed photometric data may be compared between the time of testing; the time of any prior test during the instrument's use; and the original time of manufacture of the instrument; in order to determine any gradual change in performance. The diagnostic data may be analyzed to infer the possible presence of contamination of the optics of the instrument, where the contamination may be distinguished between reasonably likely categories such as the internal deposition of dust or aerosol particles; the internal deposition of a film derived from semi-volatile vapors; or the presence of macroscopic fragments or items drawn into the optics by the suction of air flow into the sample inlet.

Optionally, the diagnostic data may be analyzed to infer the possible degradation of efficiency of the light sources, where each source providing illumination at each of the multiplicity of operational wavelengths may be tested separately. The diagnostic data may also be analyzed to infer the possible degradation of linearity of response of the instrument's photo-detectors, and that the non-linearity, if any, may be quantified in the same units as the fundamental output of the instrument.

Figure 1:
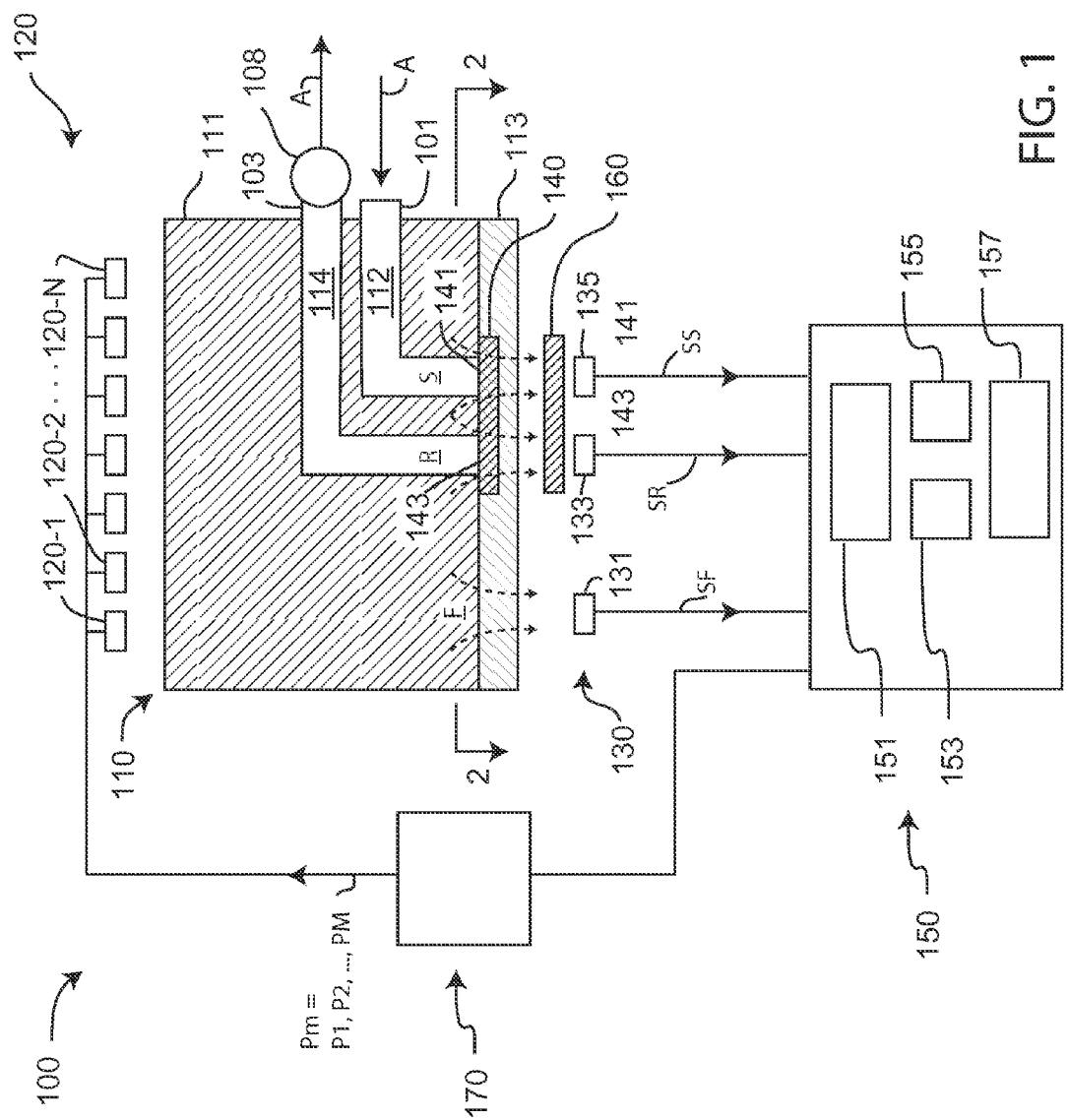
FIG. 1 a schematic of the cross-section of one embodiment of a photometric particle analyzer.
Figure 2:
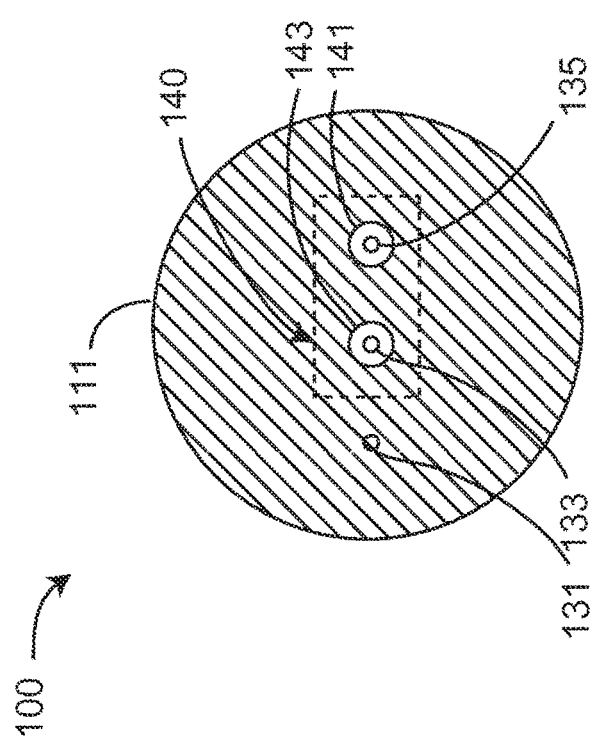
FIG. 2 is a sectional view 2-2 of FIG. 1.

FIG. 1 is a schematic of the cross-section of one embodiment of a photometric particle analyzer 100 and FIG. 2 is a sectional view 2-2 of the embodiment of FIG. 1. Photometric particle analyzer 100 is a general description of an embodiment of a photometric particle analyzer that is not meant to limit the scope of the present invention.

In certain embodiments photometric particle analyzer 100 is an analytical instrument that performs measurements on filter 140, which is positioned to collect particles from an air stream A. In certain embodiments filter 140 is illuminated by one or more light sources 120, and light that is transmitted through the filter is detected by sensors 130, which produce readings proportional to the amount of particulates deposited on filter 140. Thus, for example, sensors 140 may be calibrated to provide an estimate of fluid concentration of particulates based on light absorption through filters 140. In some instances, the calibration is linear with the logarithm of light absorption, for example. It is known that for some measurements such as optical transmission through a filter with carbon black deposits, calibrations hold for low amount of particulate loading, and that the instruments produce errors in particulate concentration as that depends on the type of particulates and their density on the filter.

Photometric particle analyzer 100 includes an optical element 110, plurality of light sources 120, sensors 130, a filter 140, a computer 150, an optional calibrated optical absorber, such as a neutral density filter 160, and a light source controller 170. As described subsequently, light from the one or more light sources 120 is transmitted through optical element 110 to individual ones of the sensors 130. Some of the sensors detect light passing through filter 140, which may include collected particles or not, and some detect light that does not pass through a filter. Optional optical absorber 160 may be placed in the optical path for certain calibration purposes.

In photometric particle analyzer 100, light sources 120 may be provide with drive currents by computer 150 according to the wavelength or wavelength range of the individual source. Thus, in one embodiment, light sources 120 may include sources having M discrete and controllable wavelengths and/or ranges of wavelengths, where each source controlled by software in computer 150. Sensors 130 detect the light from light sources 120, and the sensor output is read by computer 150. In one embodiment, the number of discrete wavelengths or wavelength ranges is selectable, either during manufacturing of the photometric particle analyzer 100 or by programming of photometric particle analyzer 100 before a measurement is made, such that the photometric particle analyzer 100 may include any number of the M discrete wavelengths or ranges of wavelengths.

Optical element 110 includes an upper portion 111 and 113, both of which are formed from a transparent material, which may be for example and without limitation glass, quartz, polycarbonate plastic, acrylic plastic, etc. Upper portion 111 includes internal passages for the flow of air, which are shown as air passage volume 112 having an inlet 101 at one end and air passage volume 114 having an outlet 103 at one end.

Filter 140 is a fibrous, porous filter material that is sandwiched between portions 111 and 113 with a filter area 141 near a second end of volume 112 and a filter area 143 near a second end of volume 114. As described subsequently, filter 140 may collect particles from particle-laden air, and is it the change in optical properties from the collected particles that form the basis of the analysis of particulate-laden air flows. Filter 140 may be furnished in the form of a continuous strip of tape, or a discrete inserted element. The use of discrete disks of filter material is used in early AETHALOMETER® instruments, and is still used in current models of the "Particle Soot Absorption Photometer" (Radiance Research, Washington). The use of continuous tape filters is used in current models of the AETHALOMETER®, the "Multi-Angle Absorption Photometer" (Thermo-Fisher, Massachusetts), the "COSMOS" analyzer (Kanomax, Japan), and others.

Outlet 103 may also be provided with a pump 108, which may be operated by computer 150, and which can draw air from inlet 101, through volume 112 and filter area 141, through filter 140, and then through filter area 143, and volume 114 to outlet 103. Photometric particle analyzer 100 may also include flow meters and/or mass flow controllers to measure or control flow F.

In one embodiment, the one or more light sources 120 are positioned in housing 110 to provide uniform, dispersed illumination to sensors 130. In certain embodiments, light sources 120 include, an array of N light emitting diode (LED) elements, individually illustrated as sources 120-$n$, where n=1 to N. In certain other embodiments, each light source 120-$n$ is an element that emits light at one of a plurality of M wavelengths or ranges of wavelengths, denoted $\lambda$(m), where m=1, 2, ... M. M may be 2, 3, 4, 5, 6, 7, 8, 9, or 10 or more wavelengths or ranges of wavelengths, ranging from the near-infrared (which may be, for example and without limitation, near 950 nm) to the near-ultraviolet (which may be, for example and without limitation, near 370 nm.

In one embodiment, each light source 120-$n$ is powered by a current Pm from light source controller 170 according to the light source wavelength. Thus, for example, each light source 120-$n$ emitting at a wavelength $\lambda$(m) is powered by current Pm. Light source controller 170 thus provides M wavelength currents for powering N light sources, according to their wavelength according to a signal from computer 150. It is therefore possible to control the wavelength of light reaching sensors 130 using computer 150.

Thus, for example, one or more of the plurality light sources 120-$n$ are selected to provide light at one of m wavelengths of light, and are each powered by the same signal Pm. Power controller 170 is thus capable of accepting an signal from computer 150 and controlling the power delivered according the wavelength of light from the plurality of light sources 120.

Examples of light sources 120 include, but are not limited to light-emitting diode ("LED") elements.

One or more light detectors, or sensors 130 shown, for example and without limitation, as 3 sensors 131, 133, and 135 positioned near portion 113. FIG. 1 also shows light paths F, S, and R, which are, respectively and for example as: path F from light sources 120 to sensor 131, as path S from light sources 120 through filter portion 141 and optional calibrated optical absorber 160 to sensor 133, and as path R from light sources 120 through filter portion 143 and optional calibrated optical absorber 160 to sensor 145. In practice, there may be other optical elements between sources 120 and sensors 130.

Examples of sensors 130 include, but are not limited to: optical sensors for the measurement of transmission through and/or reflection from particulate filters. One class of instruments is differential photometric analyzers, wherein the differences between sequential optical measurements are used to estimate particulate concentrations. Photometric particle analyzer 100 may be the differential photometric analyzer trademarked as the AETHALOMETER® (Magee Scientific Company, Berkeley Calif.) (see for example, U.S. Pat. No. 4,893,934, incorporated herein by reference); or the Multi Angle Absorption Photometer (see, for example, U.S. Pat. No. 7,038,765), or the Particle Soot Absorption Photometer (see, for example, Bond, T. C., Anderson, T. L., Campbell, D., "Calibration and intercomparison of filter-based measurements of visible light absorption by aerosols," Aerosol Science and Technology, vol. 30, pp 582-600, 1999).

In another embodiment, the one or more light sources 120 includes one light source that emits light over a wavelength range, such as a broadband source, and sensors 130 includes a corresponding detector that detects and differentiates the light according to its wavelength. Thus, for example, sensors 130 may include a spectrometer.

An optional calibrated optical absorber 160, which may be a neutral density filter, may be placed in the optical path to reduce the light reaching sensor 133 and 135 by a known, traceable and reproducible amount. In alternative embodiments, optical absorber 160 may be an optical neutral density filter, an optical interference filter, an optical reflection-based filter; or a sample filter made of glass or quartz fibers, or polytetrafluoroethylene, such as TEFLON™ (The Chemours Company, Wilmington, Del.), polycarbonate or similar material with a deposited sample of aerosol particles. These particles can be deposited on the sample filter either in the unit being calibrated itself or in a different sampler/instrument.

Photometric particle analyzer 100 also includes a computer 150 includes a processor 151 and a memory 153. Memory 153 includes programming to control the operation and received data from light sources 120 and sensors 130. Memory 153 may also store, for example and without limitation, previous sensor outputs, including but not limited to background readings (without a filter, or with a fresh filter having no deposits), the results of previous measurements, and programming to permit computer 150 to execute mathematical algorithms to convert the sensor output into some indication of one or more constituents of interest.

Computer 150 may also include display 157 to present an indication of a constituent of interest, which may be for example and without limitation, a concentration of a constituent of interest or a direct or indirect measurement related to the constituent of interest. Computer 150 may further include communications interface 155 which may be used to transmit an indication of a constituent of interest to another computer or system, either wirelessly or over a wired network. Computer 150 may also accept provide signals to control pump 108 and/or to accept input from flow controllers that may be associated with the pumps.

Computer 150 can, in addition to controlling light sources 120, control the air flow according to the speed of pump 108. Certain models can control whether the air stream flowing through the sample collecting spots contains particles, or has been pre-filtered; those models not fitted with that option can instruct the external user to attach a particle filter. Models equipped with continuous-roll tape feed can advance the filter tape, thereby inserting fresh material into the optical path; models not fitted with that option can instruct the operator to insert a fresh filter.

In certain embodiments, a baseline measurement is obtained with one or more sensors 130, where the optics and filter between light source 120 and the corresponding sensors 130 are clean. This baseline measurement may then be stored in memory 153.

When a particle-laden air sample is provided to input 101, particles are collected by filter area 141. The particle-depleted air sample then passes through filter area 143, which does not have particles for collection on that filter portion. As shown in FIG. 1, sensor 131 collects light as shown schematically as light path F, sensor 133 collects light as shown schematically as light path R, and sensor 135 collects light as shown schematically as light path S. Signals generated by one or more of sensors 131, 133, and 135 from each of these paths may be stored in memory 153 and may be used in various embodiments of the present invention, as follows. It is understood that certain methods described herein utilize the outputs from some or all of sensors 130, and thus certain methods may require that less than all of the outputs from all sensors 130 be stored in memory 153.

In one embodiment, photometric particle analyzer 100 both collects particles on filter area 141 and performs the optical measures to analyze the collected particles. In another embodiment, the air is sampled in a first device on filter 140, which is then removed from the first device and provided to a second device for optically analyzing the filter. Thus, the first and second device may both be photometric particle analyzers 100. Alternatively, a first device may is generally similar to photometric particle analyzer 100 but which does not include the optical elements, such as sources 120, sensors 130, or neutral density filter 160. Further, the second device may a photometric particle analyzer 100 or a device generally similar to photometric particle analyzer 100 but without the means to provide particles to filter 140, such as no pump 108 or volumes 112 or 114.

Lamp Feedback Detection (Light Path F)

Sensor 131 receives light from sources 120 that passes through optical element 110 without passing through volumes 112 or 114 or filter 140, as indicated as light path F. Sensor 131 provides an output SF maybe used to provide an indication of the intensity of light sources 120 to memory 153 of computer 150 which, may in turn, adjust drive currents to sources 120 to maintain a precisely fixed level of illumination intensity.

Reference Spot Detector (Light Path R)

Sensor 133 is located underneath filter area 143. Light from sources 120 passes through optical element 110, including volumes 112 and 114, and through filter area 143 and optional calibrated optical absorber, as indicated by light path R. Sensor 133 provides an output SR to memory 153 of computer 150, which may be used to provide an indication of light that passes though filter area 143. Since filter portion 141 collects nearly all of the particulates, there are little or no particulates for collection on filter area 143. Filter portion 143 is, however, subjected to a similar temperature and humidity as filter portion 141. Consequently, any effects of temperature or humidity on the optical properties of the filter material are common to all signals from which the aerosol concentration will be derived.

Sample Collecting Spot Sensing Detector (Light Path S).

Sensor 135 is located underneath filter area 141. Light from sources 120 passes through optical element 110, including volumes 112 and 114, and through filter area 141 and optional calibrated optical absorber, as indicated by light path S. Filter area 141 collects nearly all of the particulates in the air flow. Sensor 135 provides an output SS to memory 153 of computer 150, which may be used to provide an indication of light that passes through a collection of particles on filter area 141. The signal from sensor 135 is much less than that of sensor 131 or 133 due to optical absorption and/or scattering from filter area 141 and any particles collected thereon, and decreases with time as filter becomes progressively loaded with particles.

Examples of Performance Diagnosis

In general, certain embodiments of the present invention may automatically test the system response, such as the response of the light source and the light detectors, of an optical photometric particle analyzer, and provide a quantitative measure of a standardized response of the instrument that may be used to verify the analytical performance. The method may also provide a determination of the presence of contamination within the optical elements of the instrument, and enable a tentative identification of the nature of the contamination.

Certain other embodiments of the present invention may thus be used to validate the performance of instruments used for the analysis of the concentration of particles suspended in an air flow stream. This can provide for an indication of any degradation in performance due to internal contamination, and thereby remotely and automatically indicate the need for intervention and service. Both of these actions increase the utility of the instrument, by allowing it to be installed remotely and yet, by means of a data link, have its performance checked by an agent at another location, either human or automatic.

This invention achieves its result by an internal manipulation of the intensity of the light sources at one or at multiple optical wavelengths, using existing control electronics and hardware, requiring only added control software and numerical analysis of the measured results. The method produces both a validation of the instrument's analytical performance, as well as a measure of the degree and optical nature of contamination that will permit a determination of the need for intervention, remedy or cleaning.

The performance test described herein requires no physical intervention with the instrument; may be activated either by remote control or by a predetermined routine internal to the instrument; and the results may be transmitted by a data link to a remote observer or controller, either human or automatic. This permits the automatic external or self-diagnosis of an analyzer that may be located remotely, and allows for human operators or automatic systems to determine the need for intervention, remedy or cleaning.

There are several conditions which affect the performance of a photometric particle analyzer such as the AETHALOMETER®. These include, but are not limited to: contamination of the instrument's optics, degradation of the output of the instrument's light sources, and changes in the response function of the instrument.

Contamination of the instrument's optics may occur in many ways since the instruments typically include light sources that transmit light through several optical elements which permit the flow of the air stream containing the particles to be measured. The surfaces of these optical elements may gradually become contaminated with a deposit of dust from the air stream; precipitated or deposited films of compounds passing through in a semi-volatile vapor phase; or the drawing in through the suction port of macroscopic contaminants such as small pieces of foreign materials including leaf fragments, feather fragments, small insects and other items that may have been suspended in the air near the intake sampling tube of the instrument. The presence of any of these contaminants on the surfaces of the optical elements will reduce the intensity of light reaching the filtration areas of interest.

Degradation of the instrument's light sources occurs over time as the performance of the light source, such as the output of LEDs can degrade. If the source efficiency gradually decreases, then the same level of drive current power will produce less light and more heat within the LED chip element. Self-heating of the source will accentuate this effect and will lead to a loss of linearity between the drive current input and the light flux output.

A change in the instrument's response function is another source of potential error. The AETHALOMETER®, for example, derives its data from precise measurements of optical intensity signals. It is necessary to assume that the electronic signal from the detectors is indeed precisely proportional to the intensity of light incident on the detector. To validate the principle of the instrument, this assumption must be tested and verified. This validation is performed by switching the LED light sources on and then inserting into the optical path an absorbing element of known optical density, which is known to pass only a certain fraction of the light incident on it. Detector signals are measured with the calibrated absorber either inserted into the optical path or removed, and the proportionality of detector response may be verified. This process requires manual intervention and disruption of the routine operation of the instrument.

The following illustrates the use of the outputs SF, SR, and SS for testing the performance of photometric particle analyzer 100 to determine contamination of optics due to dust (section 1A), deposition of vapor films (section 1B), "macroscopic" items (section 1C), to determine degradation of optical sources (section 2), and to verify calibration and linearity of detectors (section 3). It is to be understood that each of these tests is or may be independent of the others, and that certain embodiments of the present invention require the programming and storage of information in photometric particle analyzer 100 corresponding to the test being performed. Alternatively, photometric particle analyzer 100 may be configures to perform all of the tests described subsequently.

Automatic Test Routine

The following actions may be performed automatically by the instrument in order to yield numerical data from which the performance test results may be calculated:

1. Fresh filter areas 141 and 143 are provided to photometric particle analyzer 100. If filter 140 is in the form of a roll that can be progressively moved through photometric particle analyzer 100 by the action of computer 150, the photometric particle analyzer advances filter 140 to provide a fresh, clean, particle-free areas 141 and 143. If using individually-placed filters, the photometric particle analyzer 100 will instruct the operator to insert a fresh filter 140.

2. Filtered air is provided to inlet 101, either by the photometric particle analyzer 100 instructing the operator to attach an external air filter, or by switching flow through an air filter, if one is provided with the photometric particle analyzer 100.

3. Air flow is then stopped in the photometric particle analyzer 100, which may occur, for example, by computer 150 instructing pump 108 to stop. The purpose of stopping the flow this is to eliminate any possibility of the incremental collection of any particles during the test sequence; and also to eliminate any perturbations to the filter optical properties due to active air flow.

4. Light sources 120 are illuminated according to their wavelength. In one embodiment, computer 150 instructs 170 to apply current drive levels Pm to each wavelength M in a sequence of steps, starting from a zero light source output to 100% of a maximum light source output. Thus, for example, the light sources may be driven with currents ranging from 0% to 100% of a maximum drive current level. These currents may, for example but not necessarily, be in the sequence of 0%-10%-20%-30%- . . . -90%-100%. In order to stabilize lights source 120 to their provide output at their equilibrium values, the light sources may be conditioned to their microscopic temperature, for example with the power sequence preceding each analytical power level with a certain time at 100% power, in order to heat each light source to its normal operating temperature. The power sequence may therefore be, for example but not necessarily: 0%; 100%; 10%; 100%; 20%; 100%; 30%; . . . 100%; 80%; 100%; 90%; 100%.

5. Signals SF, SR, and SS are acquired and recorded by computer 150 at each analytical power level Specifically, a diagnostic data set is recorded as a data array of signals Y for each element of the test: Y(i,m,j) where i is an index for sensor 130 (which are, for example i=1 for the signal SF, i=2 for the signal SR; and i=3 for the signal SS); m is an index representing one of each of the M wavelength channels, and j is an index representing the drive current power level (for example, j=0 for 0%, j=1 for 10%, to j=10 for 100%).

6 The diagnostic data array Y is then processed in computer 150 by an algorithm to yield a report or analytical result locally. The array Y of raw diagnostic data values may be saved, either locally within computer 150, or remotely, by transmission of data; together with other instrumental operational parameters such as date, time, operational history, total flow of air through the instrument, total flow of Black Carbon content, and any other information that may be relevant to an assessment of the performance and condition of the instrument. This data may be compared with diagnostic data previously collected at an earlier time, to determine any change in the result which may indicate a possible deterioration of the instrument; the ingress of contamination; or any other performance metric whose tracking permits assessment of the need for intervention or service.

Diagnostic data array Y may be recorded and stored in computer 150 as a baseline measurement in a diagnostic array Y0 when photometric particle analyzer 100 is first manufactured—that is with clean optics and filter. As discussed subsequently, different outputs (combinations of SF, SR, and SS) may be used for different diagnostics or calibrations. It will be understood that all of the information from diagnostic data array may thus be stored, or some subset may be stored, as needed. Diagnostic data array Y may be processed in many different ways, which may be for example and without limitation as follows:

1) Processing of Automatic Test Data to Determine Contamination of Optics.

When the instrument is first manufactured, the diagnostic routine may be performed. This will establish a baseline diagnostic data array, Y0(i,m,j). The ratio of SS (i=3) and SR (i=2) to SF (i=1) is characteristic of the geometrical relationship of the positions of the sources and detectors, and the position of the air passages 112 and 114 relative to light paths S and R. The ratios may (or may not) be different for the different wavelengths M, since the light at different wavelengths is emitted from different source elements at different positions on the source assembly. It is therefore expected that the intensity ratios SS/SF and SR/SF will be different for the different wavelengths M. These ratios will be recorded when the instrument is first manufactured and all internal optical components are scrupulously clean.

After some time of use, there may be at least three different sources of contamination which can lead to degradation of instrument performance. These include (a) dust and aerosol particles precipitated from the air stream and deposited onto the inner surfaces of the air passages 112, 114 of the optical element; (b) vapors of semi-volatile compounds that may have deposited as a film on these inner surfaces; and (c) items of "macroscopic" size such as fragments of leaves, feathers, small insects, and other items that may have been drawn into the sample air inlet by the suction of the pump. These three contaminants will affect the wavelength dependence of the relationship between the diagnostic signals SS/SF and SR/SF quite differently.

The data processing routine of computer 150 may determine the signal ratios SS/SF and SR/SF as a function of wavelength M when the optical sources are operated at their normal power level. These ratios measured at the time of the performance test will be compared against the baseline ratios stored from measurements made when the instrument was first constructed and all optical elements were perfectly clean (that is, as calculated from baseline diagnostic array Y0).

1A) Contamination Due to Dust.

Dust or precipitated aerosol particles scatter light. Dust may be present in volume 112, but will not be present in volume 114, since filter 140 removes dust from air flow A. Consequently, contamination effects will be observed primarily in the SS signal. It should be noted that the scattering of light from the inner surfaces of the air passages may affect the general distribution of light within the optical insert, and therefore the SR signal may also be affected, although to a lesser degree. This scattering of light will increase at shorter wavelengths. For particles much smaller than the wavelength of the incident light, scattering is proportional to the $5^{th}$ power of the inverse wavelength. For particles much larger than the wavelength of the incident light, scattering is proportional to the $2^{nd}$ power of the inverse wavelength. These relationships transition smoothly in such a way that the reduction in relative light intensity will be a smooth function of wavelength for the various sources M, yet increasing greatly towards the shorter wavelengths of the range spanned by the optical source.

Contamination by "dust" will therefore show a characteristic signature, being notable in the SS signal; greatly reduced if apparent at all in the SR signal; and with a steady increase in effect from longer to shorter wavelengths. A model of the effect of dust, based on these characteristics, may thus be used to generate an output indicative of the presence of dust. Thus, for example and without limitation, if the ratio of the signals SS/SF (that is, $\{Y(3,m,j)/Y(1,m,j)\}/\{Y0(3,m,j)/Y0(1,m,j)\}$ for some value of power (j) varies with wavelength ($\lambda(m)$) by an inverse power of 2 to 5, then a diagnostic signal indicating the presence of dust may be provided by computer 150.

1B) Contamination Due to Deposition of Vapor Films

Certain air samples contain pollutants in both particle and semi-volatile vapor form. Common examples of these include cigarette smoke, and the smoke from biomass combustion. These vapors can deposit onto surfaces and, over time, can create a film on the interior of the air passages within the optical insert of an AETHALOMETER®. These vapors will pass into volume 112 and 114. Consequently, there is the possibility of the deposition of a film of material on all air passages within the optical element. The optical absorption of these materials will typically be very small at longer wavelengths, from the infra-red to the yellow portion of the spectrum; but increasing very rapidly at the shorter wavelengths from the blue to the near-ultraviolet. If a film of organic material is deposited within the optics due to the passage of smokes containing volatile components, this will be expected to have a characteristic spectral signature that will aid in its identification. Thus, for example and without limitation, if the ratio of the signals SS/SF (that is, $\{Y(3,m,j)/Y(1,m,j)\}/\{Y0(3,m,j)/Y0(1,m,j)\}$ for some value of power (j) varies with wavelength ($\lambda(m)$) showing little wavelength dependence at longer wavelengths (infra-red to yellow); but strongly increasing absorption at the shortest wavelengths (blue to ultra-violet); a diagnostic signal indicating the presence of a deposited organic film may be provided by computer 150.

1C) Contamination Due to "Macroscopic" Items.

Particles of visible size can be drawn into photometric particle analyzer 100 by pump 108. Examples that have been observed include fragments of leaves; fragments of feathers; small insects; visible specks of material; and other items that could have been suspended in the air in the immediate vicinity of the sample inlet hose. If items of this nature become lodged and/or move through photometric particle analyzer 100, they may create very large perturbations is signals SR and SS that may change significantly over time. Particles of visible size are expected to only be measured in the SS signal, as the air must pass through the filter 140 before entering volume 114.

Particles of visible size may block the transmission of light equally at all wavelengths M. The characteristic signature of the presence of a piece of macroscopic contamination will be a large change in SS; relatively uniform for all wavelengths M, and no change in SR. Because of the possibility of movement of the macroscopic item under the influence of air flow, it is desirable that the diagnostic test be performed at zero air flow.

Thus, for example, if the ratio of the signals SR/SF (that is, $\{Y(2,m,j)/Y(1,m,j)\}/\{Y0(2,m,j)/Y0(1,m,j)\}$ for some value of power (j) varies has little variation (that is, for example and without limitation, from 0.99 to 1.01), and the ratio of the signals SS/SF (that is, $\{Y(2,m,j)/Y(1,m,j)\}/\{Y0(2,m,j)/Y0(2,m,j)\}$ for some value of power (j) has a large variation (that is, for example and without limitation, less than 0.10) then a diagnostic signal indicating the presence of macroscopic particles may be provided by computer 150.

2) Processing of Automatic Test Data to Determine Degradation of Optical Sources The detector signal SF is expected to be a monotonic function of the power level (that is, j index) although not necessarily perfectly linear, depending on the internal characteristics of the light source 120 elements which may include a temperature dependence affected by self-heating. The original signals $SF_0(m,j)$ will be recorded for each M wavelength at each power level, j. At the time of subsequent testing, the same routine will be followed and the array of signals SF(m,j) will be recorded. Other effects such as changes in relative mechanical positioning or alignment; aging of the transparent material of the optical element; etc.; may lead to overall changes in the scaling magnitude of these signals. However, the progression of intensities should not change as a function of drive current power level j. Changes in the emission characteristics of the sources may be detected by monitoring the intensities at the time of subsequent testing relative to the intensities measured at the time of the initial measurement, and interpreting the change in this relative parameter as a possible indication of the degradation of sources. This may be expressed by the ratio of intensities at power level, j, relative to a baseline at a low power level, such as j=1 as $\{Y(1,m,j)/Y0(1,m,j)\}/\{Y(1,m,1)/Y0(1,m,1)\}$. This ratio is expected to be equal to 1 if the optical source output as a function of drive current has not changed from the time of manufacture to the time of test. If, however, the sources have become degraded, this is usually exhibited as a loss in efficiency of conversion of electrical current to luminous intensity. This means that at higher drive current power levels, the light output from a degraded source will not increase relative to a low drive power level as much as it did when the components were new.

This test can be performed for all light sources 120, as a function of wavelength m across the range of drive current power levels j to determine any changes in performance of the optical source elements. In this way, aging or loss of intensity of the sources can be detected. Thus, for example and without limitation, if $\{Y(1,m,j)/Y0(1,m,j)\}/\{Y(1,m,1)/Y0(1,m,1)\}$ is greater than 1.01 or less than 0.99 then a diagnostic signal indicating the degradation of optical source 120 may be provided by computer 150.

3) Processing of Automatic Test Data to Verify Calibration and Linearity of Detectors Sensors 131, 133, and 135 each receive light emanating from the source assembly. Sensors 133 and 135 are located underneath filter 140; sensor 131 is located to the side of filter 140. It was noted above that the presence of contamination in the optical element is expected to reduce the intensity signals SS and SR channels relative to SF, and with a wavelength dependence that may be indicative of the nature of the contamination. Consequently, it is not possible to use the relative intensities of signals SF, SR, or SF at any given drive current power level to deduce the detectors' performance, since the absolute intensities will be affected by the presence of contamination.

However, if a calibrated optical element (for example neutral density filter 160) is provided in light paths R and S, the intensity of light reaching sensors 133 and 135 will be reduced, while the intensity of light reaching sensor 131 will be unaffected. The following routine may then be performed on a brand-new instrument to establish a baseline response of sensors 130, where deviations from the original values may be interpreted as changes in the performance of sensors 130. Furthermore, comparison of the results from the subsequent automatic diagnostic routine with those from the initial optical calibration routine using the known optical absorber (for example neutral density filter 160), permit a verification of the continuing performance of the sensors 130 that may be referenced back to the known and traceable properties of the calibrator.

The following tests are performed at all wavelengths M, in sequence.

i) As an initial factory calibration, the optical drive current level Pm is ramped up in steps from zero to its maximum level. As described above, there may for example but not necessarily be a routine in which the optical sources are conditioned at 100% power before being reverted for testing at the $j^{th}$ level power. The signals Y0(i,m,j) are recorded for each sensor 130. A mathematical relation, such as a polynomial fit, will be calculated for the relationship between Y0(i,m,j) and the drive current Pm for each sensor 130 at each wavelength m ($\lambda(m)$). This fit may or may not be perfectly linear; and may or may not contain a zero offset intercept representing the digital signal reported to the electronics even at zero optical drive current. After subtraction of the zero offset, the functions may then be averaged over the number of all sensors 130 to yield a composite response of the average sensor 130 as a function of drive current. The deviations between any individual detector signal Y0(i,m,j) relative to the average $Y_{0,av}(j)$ are calculated and saved.

ii) Neutral density filter 160 is then inserted into paths R and S (that is, for i=2 and 3); the source intensity step ramp is repeated; and the signals are recorded. In this case, the signals from the "shaded" sensors 133 and 135 are reduced relative to the signal from the "unshaded" sensor 131. The same mathematical relations, such as the polynomial fits, are performed on data Y(i,m,j) as a function of drive current Pm(j). After subtraction of zero offset intercepts, the polynomial slope parameters for sensor 131 (i=1) are be expected to be substantially identical to the previous test; while the polynomial slope parameters for sensors 133 and 135 detectors R and S will exhibit coefficients reduced by the effect of the neutral density filter 160. The relationship of this reduction in intensity to the known and traceable property of neutral density filter 160 provides a calibration of the relationship between optical signal reported and a known degree of Optical Density. This constitutes the primary photometric calibration photometric particle analyzer 100. This relation may be different for the different wavelengths m, but is expected to be repeatable.

iii) At each optical drive current power level Pm(j), the relative values of the "shaded" to "unshaded" signals, such as the ratio {Y(i,m,j)/Y(1,m,j)} are calculated after subtraction of the zero offset intercepts. From the polynomial fit parameters, the proportional increase in drive current that would be required to bring the signal to its previous level may be calculated, before the insertion of neutral density filter 160. This proportion factor is calculated for the "shaded" signal R and S for the lower ranges of drive power (small j's) such that the calculated drive current remains within the operating range. The average of this calculation establishes the relationship between the known degree of absorption due to the Optical Density of neutral density filter 160, and the proportional increase in optical source drive current required to overcome the absorption and restore the signals to their previous levels. This constitutes the working relationship of the transfer function between an instrumental control parameter—change in the optical drive current I—and the effect of a known, calibrated and traceable external calibrating element in the form of an optical absorber; as mediated by the response characteristics of the conversion of electrical current to light intensity by the sources, and the detection of the light by the photo-detectors. This relationship will be established for the instrument at the time of initial manufacture when all components are clean and new.

At the time of subsequent test, step (i) will be repeated: the optical drive current level Pm is ramped up in steps from zero to its maximum level. As described above, there may for example but not necessarily be a routine in which the optical sources are conditioned at 100% power before being reverted for testing at the $j^{th}$ level power. The signals Y2(i,m,j) are recorded for each sensor 130. A mathematical polynomial fit may then be calculated for the relationship between Y2(i,m,j) and the drive current Pm for each sensor 130 at each wavelength m.

The effects of degradation of the optical sources may reduce the intensity of the signal Y2 (1,m,j) from sensor 131, as a function of drive current power Pm for the various wavelength sources M. The relationship between emitted intensity and drive current Pm cannot be expected to remain constant.

The effects of contamination may reduce the magnitude of the signals from the S and R detectors relative to the emitted source intensity, to a degree that may differ between the three detectors and which will be a function of wavelength. However, the fractional loss of signal intensity due to contamination is not expected to be a function of the optical intensity level itself, i.e. will not be a function of optical drive current Pm. Therefore, the relative proportionality between any of the detectors' signals and their geometric mean will not be expected to be a function of drive level Pm, unless there is a loss of linearity.

The mathematical processing will therefore consist of calculating a polynomial fit to Y2(i,m,j) as a function of Pm(j), subtracting the zero offset intercept, and calculating the geometric mean of the signals at each power level Pm(j). The ratio of each individual signal to this mean {Y2(i,m,j)/Y2(mean) (m,j)} may be a constant factor but should not be a function of drive level, j, unless there is the onset of non-linearity in one of the detectors.

Any deviation in a signal detector's output as a function of optical intensity—i.e. any non-linearity—can be converted to an equivalent fractional increase in optical drive that would be necessary to overcome it, given the mathematical fit to signal versus drive current. This, in turn, can be converted to an equivalent effect of change in intensity due to the effect of a known, calibrated and traceable amount of Optical Density due to the insertion of an optical absorber (for example a neutral density filter 160). In this way, any deviation in linearity of any photo-detector can be expressed in terms that can be related to an external standard. The linearity of the system can be remotely checked and verified to meet required performance standards by means of the operations described above of increasing, or ramping, the optical drive current through a sequence of steps and recording the signals from the photo-detectors.

Thus, for example and without limitation, if {Y2(i,m,j)/Y2(mean) (m,j)} is approximately a constant (for example varies by less than 1% for all drive levels j), then a diagnostic signal indicating the onset of non-linearity in one of the sensors 130 is provided by computer 150.

One embodiment of each of the methods described herein is in the form of a computer program that executes on a processing system, e.g., on one or more processors. Thus, as will be appreciated by those skilled in the art, embodiments of the present invention may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code segments embodied in the medium. Any suitable computer readable medium may be used including a magnetic storage device such as a diskette or a hard disk, or an optical storage device such as a CD-ROM.

It will be understood that the steps of methods discussed are performed in one embodiment by an appropriate processor (or processors) of a processing (i.e., computer) system executing instructions (code segments) stored in storage. It will also be understood that the invention is not limited to any particular implementation or programming technique and that the invention may be implemented using any appropriate techniques for implementing the functionality described herein. The invention is not limited to any particular programming language or operating system.

It should further be appreciated that although the coding of the computer has not be discussed in detail, the invention is not limited to a specific coding method. Furthermore, the invention is not limited to any one type of network architecture and method of encapsulation, and thus may be utilized in conjunction with one or a combination of other network architectures/protocols.

Reference throughout this specification to "one embodiment," "an embodiment," or "certain embodiments" means that a particular feature, structure or characteristic described in connection with the embodiment is included in at least one embodiment of the present invention. Thus, appearances of the phrases "in one embodiment," "in an embodiment," or "in certain embodiments" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Thus, while there has been described what is believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

We claim:

1. A method of testing a photometric particle analyzer, where the photometric particle analyzer includes one or more light sources each emitting light at a corresponding wavelength or a corresponding range of wavelengths, where each light source has a controllable intensity, a filter to collect particles, a first light path from the light source through a collecting portion of the filter that may be exposed to particle laden-air to a first sensor that produces a first signal, a second light path from the light source through a reference portion of the filter to a second sensor that produces a second signal, and a third light path from the light source to a third sensor without passing through the filter, where said third sensor produces a third signal, said method comprising:

selecting the number of wavelengths or ranges of wavelengths of the one or more light sources;

obtaining a baseline measurement of the first, second, and third signals, where said obtaining obtains with first light path, second light path, and third light path, in the absence of particles, and where said obtaining includes:

operating the light sources at the selected number of wavelengths or ranges of wavelengths, and recording the baseline measurement;

using the photometric particle analyzer to sample particle-laden air;

obtaining a test measurement of the first, second, and third signals for the photometric particle analyzer after using the photometric particle analyzer to sample particle-laden air by:

replacing the collecting portion of the filter with a collecting portion that has not been previously used to collect particles, operating the light sources at the selected number of wavelengths or ranges of wavelengths, and recording the test measurement; and generating an output from a comparison of said baseline measurement and said test measurement, where said output is a diagnostic of the operation of the photometric particle analyzer.

2. The method of claim 1, where the wavelengths or ranges of wavelengths includes wavelengths from the near-infrared to the near-ultraviolet.

3. The method of claim 1, where the wavelengths or ranges of wavelengths includes 1, 2, 3, 4, 5, 6, 7, 8, 9, or 10 wavelengths or ranges of wavelengths.

4. The method of claim 1, where the reference portion of the filter and said collecting portion of the filter have approximately the same temperature and moisture content.

5. The method of claim 1, where the photometric particle analyzer includes a computer having a memory for storing said baseline measurement.

6. The method of claim 1, where said generating includes comparing said baseline measurement and said test measurement against a model of the effect of one or more types of contamination, and where said output is an indication of a likely type of contamination.

7. The method of claim 6, where said type of contamination includes dust, vapor films or macroscopic items.

8. The method of claim 1, where said operating the light sources includes operating the light sources at a range of light source output.

9. The method of claim 8, where said range of light source output is between 0 percent and 100 percent of a maximum light source output.

10. The method of claim 1, where said obtaining a test measurement of the first, second, and third signals for the photometric particle analyzer after using the photometric particle analyzer to sample particle-laden air includes:

inserting an optical absorber in the second and third light paths while obtaining said test measurement, and where said generating an output includes determining a change in a calibration of the second and third sensor from the test measurement and reporting a change in the calibration.

11. The method of claim 10, where said optical absorber includes one or more of an optical neutral density filter, an optical interference filter, or an optical reflection-based filter.

12. The method of claim 10, where said optical absorber includes a sample filter with a deposited sample of aerosol particles.

13. The method of claim 12, where said sample filter is made of glass or quartz fibers, polytetrafluoroethylene, or polycarbonate.

14. The method of claim 10, where said generating an output includes determining a change in the output of one or more of said one or more light sources, and where said reporting includes reporting the change in the output of the one or more light sources of the one or more light sources.

15. The method of claim 10, where said reporting is reporting the calibration of one or more of the first, second, or third sensor.

16. The method of claim 1, wherein said one or more light sources includes one light source emitting light over a range of wavelengths, and where said first sensor is a spectrometer, said second sensor is a spectrometer, and said third sensor is a spectrometer.

17. A method of testing a photometric particle analyzer having one or more light sources each emitting light at a corresponding wavelength or a corresponding range of wavelengths, optics, a filter that may collect particulates, and sensors, including a first sensor, a second sensor and a third sensor, and a stored baseline measurement of one or more of the sensors obtained with clean optics and filter between said light source and said one or more sensors, said method comprising:
selecting the number of wavelengths or ranges of wavelengths of the one or more light sources;
providing light from the one or more light sources through a collecting portion of the filter that may be exposed to particle laden-air to the first sensor that produces a first signal;
providing light from the one or more light sources through a reference portion of the filter to the second sensor that produces a second signal;
providing light from the one or more light sources through the third sensor without passing through the filter, where said third sensor produces a third signal; and
generating an output from a comparison of said first signal, said second signal, said third signal and the stored baseline measurement,
where said output is a diagnostic of one or more of the first signal, the second signal, and the third signal of the photometric particle analyzer.

18. The method of claim 17, where the wavelengths or ranges of wavelengths includes wavelengths from the near-infrared to the near-ultraviolet.

19. The method of claim 17, where the wavelengths or ranges of wavelengths includes 1, 2, 3, 4, 5, 6, 7, 8, 9, or 10 wavelengths or ranges of wavelengths.

20. The method of claim 17, where the reference portion of the filter and said collecting portion of the filter have approximately the same temperature and moisture content.

21. The method of claim 17, where said generating includes comparing the stored baseline measurement and the second signal against a model of the effect of one or more types of contamination, and where said output is an indication of a likely type of contamination.

22. The method of claim 21, where said type of contamination includes dust, vapor films or macroscopic items.

23. The method of claim 17, where said providing light includes providing light over a range of intensities.

24. The method of claim 23, where said range of light source outputs is between 0 percent and 100 percent of a maximum light source output.

25. The method of claim 17, further comprising:
inserting an optical absorber between said collecting portion of the filter and said first sensor and between said reference portion of the filter and said second sensor,
where said generating an output includes determining a change in a calibration of the second and third sensor from the test measurement and reporting a change in the calibration.

26. The method of claim 25, where said optical absorber includes one or more of an optical neutral density filter, an optical interference filter, or an optical reflection-based filter.

27. The method of claim 25, where said optical absorber includes a sample filter with a deposited sample of aerosol particles.

28. The method of claim 27, where said sample filter is made of glass or quartz fibers, polytetrafluoroethylene, or polycarbonate.

29. The method of claim 25,
where said reporting is reporting a change in the output of one or more of the one or more light sources.

30. The method of claim 25, where said reporting is reporting the accuracy of the calibration of one or more of the first, second, or third sensor.

31. The method of claim 17, wherein said one or more light sources includes one light source emitting light over a range of wavelengths, and where said first sensor is a spectrometer, said second sensor is a spectrometer, and said third sensor is a spectrometer.

* * * * *